United States Patent [19]

Monte

[11] Patent Number: 5,942,264
[45] Date of Patent: *Aug. 24, 1999

[54] ICE CREAM CONTAINING A LACTOSE ENZYME COMPOSITION AND METHOD

[76] Inventor: Woodrow C. Monte, 6411 S. River Dr., No. 65, Tempe, Ariz. 85283

[ * ] Notice: This patent is subject to a terminal disclaimer.

[21] Appl. No.: 09/006,473

[22] Filed: Jan. 13, 1998

Related U.S. Application Data

[63] Continuation-in-part of application No. 08/707,732, Sep. 3, 1996, Pat. No. 5,707,843.
[51] Int. Cl.$^6$ ............................... A23C 9/12; A23G 9/00
[52] U.S. Cl. ............................... 426/42; 426/61; 426/101
[58] Field of Search ..................................... 426/521, 101, 426/565, 42, 61

[56] References Cited

U.S. PATENT DOCUMENTS

| | | | |
|---|---|---|---|
| 4,374,861 | 2/1983 | Trzecieski | 426/42 |
| 4,931,300 | 6/1990 | Monte | 426/335 |
| 4,959,227 | 9/1990 | Amer | 426/35 |
| 5,156,875 | 10/1992 | Monte | 426/532 |
| 5,389,391 | 2/1995 | Monte | 426/335 |

*Primary Examiner*—Keith D. Hendricks
*Attorney, Agent, or Firm*—Tod R. Nissle, P.C.

[57] ABSTRACT

An enzyme—ice cream composition in which a sterilized acid-sensitive lactase enzyme hydrolyzes lactose after the ice cream is frozen to a temperature less than twenty degrees Fahrenheit.

6 Claims, No Drawings

ICE CREAM CONTAINING A LACTOSE ENZYME COMPOSITION AND METHOD

This application is a CIP of application Ser. No. 08/707,732, filed Sep. 3, 1996, now U.S. Pat. No. 5,707,843.

This invention relates to enzyme compositions.

More particularly, the invention relates to an enzyme composition which can be added to a pasteurized or sterilized dairy product without contaminating the dairy product.

In another respect, the invention relates to a method which, in comparison to prior art procedures, significantly reduces the cost of producing reduced-lactose dairy products.

In a further respect, the invention relates to a method which continues to reduce the lactose content of a dairy product after the dairy product has been ingested.

In still another respect, the invention relates to a method which inexpensively hydrolyzes all or part of the lactose in a dairy product.

In yet a further respect, the invention relates to an acidic composition which is used to hydrolyze lactose in ice cream and which produces unexpected and surprising results by incorporating an acid sensitive lactose—hydrolyzing yeast enzyme to hydrolyze all of the lactose when the ice cream is frozen to less than twenty degrees fahrenheit.

Reduced-lactose content dairy products are well known and are utilized by lactose intolerant individuals. Such products ordinarily are produced by one of two methods.

The first method for reducing the lactose content of a dairy product comprises adding lactase enzyme to a milk product and then heating the milk product at an elevated temperature in excess of about 140 degrees Fahrenheit for about three hours to allow the enzyme to hydrolyze lactose in the milk product. There are several disadvantages associated with this method. First, relatively large amounts of the lactase enzyme are required. The milk product typically must include 200 to 1000 parts per million of lactase enzyme. Lactase enzyme is costly. One gallon of lactase enzyme liquid costs about $65.00; one pound of solid lactase enzyme costs about $120.00. Second, when the milk product is heated to an elevated temperature, the growth of unwanted bacteria and the production of off flavors can sometimes occur. Third, enzymes typically are laced with bacteria, exacerbating the growth of bacteria when the milk product is heated at an elevated temperature. Fourth, often only a 70% reduction of the lactose to glucose and galactose is achieved by the enzyme.

The second method for reducing the lactose content of a dairy product comprises adding lactase enzyme to a milk product and then cooling the milk product to below 45 degrees Fahrenheit for twelve to eighteen hours to allow the enzyme to hydrolyze lactose in the milk product. There are several disadvantages associated with this method. First, relatively large amounts of the lactase enzyme are required. Lactase enzyme is, as noted, costly. Second, maintaining dairy products at refrigerated temperatures is an added cost to any dairy operation. Third, often only a 70% enzymatic reduction of the lactose to glucose and galactose is achieved during refrigeration of the dairy products. Fourth, the enzyme typically functions as a carrier which introduces foreign microbes into the milk product.

Accordingly, it would be highly desirable to provide an improved method and composition which would reduce the cost of enzyme, would reduce other costs associated with reducing the lactose content of a dairy product, and would achieve a significantly greater reduction of lactose than prior art processing methods.

Therefore, it is a principal object of the invention to provide an improved composition and process for reducing the lactose in a dairy product.

A further object of the invention is to provide an improved food composition which can, after a dairy product has been pasteurized or sterilized, be combined with a dairy product to reduce the concentration of lactose in the dairy product.

Another object of the invention is to provide an improved food composition and process which economically hydrolyzes lactose in a dairy product.

Still a further object of the invention is to provide an improved method for insuring the hydrolysis of all the lactose in a dairy product.

Yet another object of the invention is to provide an improved method for hydrolyzing lactose in a frozen shake dairy product while it is frozen for storage, while it is being thawed to produce a milk shake which can be ingested, and while the product is being ingested.

Yet still a further object of the invention is to provide an improved method for commercially sterilizing an enzyme.

These and other, further and more specific objects and advantages of the invention will be apparent to those skilled in the art from the following detailed description thereof.

Briefly, I have discovered a chemical method to make a commercially sterile powder enzyme composition for combination with a lactose-containing liquid which has been heated to a selected temperature for a time sufficient to at least pasteurize the lactose-containing liquid. The enzyme composition hydrolyzes lactose to glucose and galactose and consists of from 4% to 20% by weight of an edible acid for adjusting the pH of the enzyme composition to within the range of about 2.0 to 6.0 when the composition is hydrated; from 2% to 20% by weight of a buffering salt to facilitate maintenance of the pH in the range of 2.0 to 6.0; from 0.02% to 10% by weight of an antimicrobial agent selected from the group consisting of sorbic acid, benzoic acid, sodium benzoate, potassium sorbate, sodium sorbate, and potassium benzoate; and, from 14% to 93% by weight of an enzyme to hydrolyze lactose. The enzyme powder composition can be hydrated and include from 50% to 99% (preferably 79% to 98%) by weight of water. The pH of the hydrated enzyme food composition is from 1.5 to 6.0, preferably 2.0 to about 4.6. For purposes of the present specification, the term "dairy product" is defined to include a liquid or solid food composition containing lactose; and, the term commercially sterile means that a powder or liquid enzyme composition or a dairy product does not include living pathogenic bacteria, but may include living non-pathogenic bacteria. Pathogenic bacteria destroy healthy cells and prevent an individual's body from functioning properly.

Any food grade emulsifier or wetting agent or surfactant can, if desired, be used in the powder enzyme composition for present emulsification purposes and combinations for emulsifiers are used if desired. Any of the long fatty acid glycerol emulsifiers can be used, which normally have a C-12 to C-20 esterified chain. Typical among these are glycerol-lactopalmitate or the stearate. Alternately, the propylene derived emulsifiers may be used, such as propylene glycomonosterate, or oleate, palmitate, and myristate. Likewise, the "Span" series of emulsifiers may be used. These are well-known emulsifiers and are fatty acid partial esters of the sorbitol anhydrides (or sorbitan). One well known emulsifier is the "Tween" series of polyoxyethylene derivatives of fatty acid partial esters of sorbitol anhydride. Tween 80 and Atmos 300 are often used in combination. The well known Atmos series of mono and diglycerides may be used. Also, lecithin is a suitable emulsifier or sodium lauryl sulfate is a suitable surfactant. The amount of the emulsifier is chosen to suit the particular powder enzyme composition, and generally ranges from about 0.01 % to 10% by weight.

The enzyme composition is provided in a powdered form which preferably, but not necessarily, has a relatively low moisture content. The moisture content is, as is the case for many powdered formulations, preferably at least below 4% by weight and more preferably below 3% by weight. Such low moisture content provides a product having a shelf life of at least one year shelf stability at ambient conditions if hermetically sealed.

The powdered form of the enzyme composition may be reconstituted with a liquid. The liquid form of the enzyme composition of the invention can be heated to pasteurize or sterilize the composition, but need not be so heated because the hydrated enzyme composition is chemically sterilized by the edible acid—buffer—antimicrobial agent combination.

As noted above, from 4% to 20% by weight of an edible acid is included in the powder enzyme composition to adjust the pH of the enzyme composition when the composition is hydrated. The edible acidulant can, for example, be malic acid, acetic acid, citric acid, lactic acid, sodium acetate, fumaric acid, or an acidic salt such as sodium acetate in order to adjust the pH within the range of 1.5 to 6.0, preferably about 2.0 to 4.6 when the powder composition is hydrated. This pH is critical. Any pH in excess of about 6.0 is unacceptable because such allows greater microbial activity and minimizes the antimicrobial effects of sorbates and benzoates utilized in the invention. A pH equal to or less than 4.6 is preferred because the antimicrobial activity of the sorbates and benzoates is enhanced to insure, along with the buffering salt, a chemically sterilized enzyme composition which is substantially devoid of microbes.

From 2% to 20% by weight of a buffer, preferably a salt, in the powder enzyme combination functions to maintain the pH in the range of 2.0 to 6.0. Examples of buffering salts include, by way of example and not limitation, anhydrous disodium phosphate, dihydrated disodium phosphate, dipotassium phosphate, sodium citrate, potassium salts, calcium salts, and/or sodium salts.

From 0.02% to 10% by weight of an antimicrobial agent selected from the group consisting of sorbic acid, benzoic acid, sodium benzoate, potassium sorbate, sodium sorbate, and potassium benzoate functions in combination with the edible acid and buffering salt to produce an antimicrobial enzyme composition.

From 14% to 93% by weight of a lactose-hydrolyzing enzyme is included. By way of example, and not limitation, such enzymes can include lactase (fungal lactase for example), cellulase, and protease.

If desired, a powder filler like maltodextrin, or some other carbohydrate can be utilized when preparing the enzyme powder of the invention. The powder filler can comprise from 0.1% to 75% by weight of the enzyme powder composition. When a filler is added to the powder enzyme composition, it, as would be appreciated by those of skill in the art, proportionally reduces the weight percent of enzyme, acidulant, antimicrobial agent, and buffer salt in the food enzyme powder composition.

The powder enzyme composition is reconstituted with any desired edible liquid, including, for example, an alcohol. The powder is ordinarily partially dissolved and partially suspended in the resulting liquid form of the invention. The reconstituting liquid ordinarily will be water.

The antimicrobial activity of sorbic and benzoic acid is due primarily to the undissociated acid molecule. Antimicrobial activity is therefore pH dependent and the estimated activity at any pH can be estimated as shown below in Table 1.

TABLE 1

EFFECT OF pH ON DISSOCIATION

| pH | Percent Undissociated Acid | |
|---|---|---|
| | Sorbic | Benzoic |
| 3 | 98 | 94 |
| 4 | 86 | 60 |
| 5 | 37 | 13 |
| 6 | 6 | 1.5 |
| 7 | 0.6 | 0.15 |

Instead of chemically commercially sterilizing the lactose-hydrolyzing enzyme(s) utilized in the invention to selectively kill pathogenic bacteria while allowing other living bacteria to remain, the enzyme composition can be commercially sterilized by filtering the composition through a membrane with 0.45 microns openings to removed bacteria. Or, such a membrane filtration process can be utilized prior to combining the enzyme with the acidulant—buffer—antimicrobial agent chemical sterilizing composition described above. One disadvantage of the membrane sterilization process is that the resulting sterilized enzyme runs the risk of contamination. In contrast, when the chemical sterilizing composition described herein is utilized, the enzymes are continuously protected by that sterilizing composition until they are incorporated in a dairy product. Consequently, the chemical sterilization composition of the invention is preferred.

In another embodiment of the invention, I have discovered a method for preparing a pasteurized lactose-containing liquid in which the concentration of lactose is decremented and which provides enzymes which continue to function in the human digestive tract after ingestion of the liquid. The method includes the steps of providing a dairy product; providing a chemically commercially sterilized enzyme composition of the type described above; heating the dairy product to a selected temperature for a time sufficient to at least pasteurize the dairy product; combining the chemically sterile enzyme composition with the pasteurized dairy product to produce an enzyme—dairy product combination; packaging the enzyme—dairy product combination; and, storing the packaged enzyme—dairy product combination produced in step (e) to permit the enzyme to hydrolyze lactose in the enzyme—dairy product.

One advantage of the method of the invention is that a much smaller amount of enzyme can be utilized. Prior art processes typically require from 200 to 1000 parts per million of enzyme for dairy products like whole or skim milk, each of which contains about 4.5% by weight of lactose. Human milk contains about 10% by weight lactose. While the process of the invention can, if desired, utilize such high concentrations of enzyme, ordinarily only 1 to 150 parts per million, preferably 5 to 75 parts per million, of enzyme is employed.

A second advantage of the method of the invention is that while prior art lactose reduction procedures ordinarily achieve only a seventy percent reduction of the lactose concentration in a dairy product, the process of the invention can achieve a one hundred percent reduction in the lactose concentration. The lactose-hydrolyzing enzyme continues to function after the dairy product treated with the enzyme composition of the invention is packaged, after the dairy product is cooled or frozen (some product often continues to exist in the liquid state after the product is frozen, permitting the enzyme to continue gradually to hydrolyze lactose in frozen products), after the dairy product is, if necessary, thawed or warmed and served, and when the product is initially introduced into the digestive tract of an individual. The period of time required to hydrolyze substantially all of the lactose in a diary product for a given concentration in parts per million of lactose-hydrolyzing enzyme can be estimated quite accurately once the storage temperature of the dairy product is known. For example, if the dairy product is whole milk and will be stored at 35 to 40 degrees Fahrenheit, then, depending on the concentration of lactose-hydrolyzing enzyme, it may take from two to five days to hydrolyze substantially all of the lactose in the whole milk. If, on the other hand, the dairy product is a milk shake mixture which consists principally of milk and sugar and which may, for example, be refrigerated for twenty-four hours, frozen and stored for weeks or months at a temperature of about twenty-five degrees Fahrenheit, then, depending on the concentration of lactose-hydrolyzing enzyme, it may take from about three days to a week or more to hydrolyze substantially all of the lactose in the milk shake mixture. As used herein, substantially all of the lactose in a dairy product is hydrolyzed when 98% or more of the lactose is hydrolyzed.

A third advantage of the method of the invention is that a dairy product need not be heated or cooled for extended times immediately after the enzyme composition is added. Instead, normal processing procedures for the dairy product can be continued. Heating the dairy product to a pasteurization or sterilization temperature after the enzyme composition is added is counterproductive in practicing the invention because enzymes are deactivated at pasteurization and sterilization temperatures. As used herein, a dairy product is deemed to be "at least pasteurized" either if it is heated to a temperature for a time sufficient to pasteurize it or if it is heated to a temperature for a time sufficient to sterilize it.

A fourth advantage of the method of the invention is that it allows an enzyme to be added after the dairy product is pasteurized or sterilized. This is a particularly unusual aspect of the invention since the prior art teaches squarely against adding enzymes or other possible contaminants to a milk product after the milk product is pasteurized or sterilized. Buffers, acidulants, and benzoates or sorbates have been long utilized in a variety of food products, but apparently have never been combined to chemically sterilize enzymes and produce a composition which is introduced into a pasteurized dairy product to accomplish complete post-pasteurization lactose hydrolysis in accordance with the method of the invention.

The pH stability of the enzyme composition of the invention is increased by utilizing a buffer system. The buffer system resists any change in the pH of the enzyme composition for one minute up to about three hours, preferably for at least about five to thirty minutes, after the enzyme composition is hydrated to allow a sufficient period of time for at least the pathogenic bacteria in the composition to be killed. The buffer system is important because the water utilized to hydrate the enzyme composition may include pathogenic bacteria or non-pathogenic bacteria. In particular, buffering salts are presently preferably preferred in the practice of the invention and can, by way of example and not limitation, include anhydrous disodium phosphate, dihydrated disodium phosphate, dipotassium phosphate, sodium citrate, potassium salts, calcium salts, and/or sodium salts.

The pH of the resulting hydrated enzyme composition is equal to or less than about 6.0, and under the most preferred conditions is less than about 4.6. The low pH has been found important in providing an enzyme composition which has a high antimicrobial capacity and which can be added to a pasteurized or sterilized milk product without microbially contaminating the milk product.

In another embodiment of the invention, I have discovered a method for commercially sterilizing an enzyme. The method includes the steps of forming a chemical sterilization composition by admixing water, an edible acid, a buffer, and an antimicrobial agent selected from the group consisting of sorbic acid, benzoic acid, sodium benzoate, potassium sorbate, sodium sorbate, and potassium benzoate; and, mixing the enzyme with the chemical sterilization composition to form an enzyme sterilization composition. The enzyme sterilization composition has a pH in the range of 2.0 to 4.6 and includes 50% to 99% (preferably 79% to 98%) by weight of water; 0.1% to 6.0% by weight of the edible acid; 0.001% to 5.0% by weight of the buffer; 0.01% to 6.0% by weight of the antimicrobial agent; and, 0.001% to 45% (preferably 0.1% to 20%) by weight of the enzyme. The edible acid, buffer, and enzyme can be of the types earlier discussed herein.

In still a further embodiment of my invention, I have discovered an improved method for preparing and storing a pasteurized lactose-containing liquid in which substantially all of the lactose is hydrolyzed prior to ingestion of the liquid by a lactose intolerant individual. The method includes the steps of providing a dairy product; and, chemically commercially sterilizing a lactose-hydrolyzing enzyme by admixing from 50% to 99% (preferably 79% to 98%) by weight of water, from 0.1 to 6% by weight of an edible acid for adjusting the pH of the enzyme composition within the range of about 2.0 to 6.0, from 0.001% to 5% by weight of a buffer to facilitate maintenance of the pH in the range of 2.0 to 6.0, from 0.01% to 6% by weight of an antimicrobial agent selected from the group consisting of sorbic acid, benzoic acid, sodium benzoate, potassium sorbate, sodium sorbate, and potassium benzoate, and, from 0.001% to 45% (preferably 0.1% to 20%) by weight of the lactose-hydrolyzing enzyme to form a commercially sterile enzyme composition. The dairy product is heated to a selected temperature for a time sufficient to at least pasteurize the dairy product; a selected quantity of the commercially sterile enzyme composition is combined with the pasteurized dairy product to produce an enzyme—dairy product combination containing from five to one hundred and fifty parts per million of said lactose-hydrolyzing enzyme; the enzyme—dairy product combination is packaged; and, the packaged enzyme—dairy product combination produced in step (e) is stored for a length of time sufficient to permit the enzyme to hydrolyze substantially all of the lactose in the enzyme—dairy product prior to ingestion of the enzyme—dairy product by an individual. The packaged enzyme—dairy product can be stored for a period of time in the range of two to seven days, or longer, prior to ingestion. The edible acid, buffer, and enzyme can be of the types earlier discussed herein.

In yet another embodiment of my invention, I have discovered an improved method for preparing and storing a pasteurized lactose-containing frozen shake product in which substantially all of the lactose is hydrolyzed prior to ingestion of the product by a lactose intolerant individual. The method includes the steps of providing a dairy product; and, chemically commercially sterilizing a lactose-hydrolyzing enzyme by admixing from 50% to 99% (preferably 79% to 98%) by weight of water, from 0.1 to 6% by weight of an edible acid for adjusting the pH of the enzyme composition within the range of about 2.0 to 6.0, from 0.001% to 5% by weight of a buffer to facilitate maintenance of the pH in the range of 2.0 to 6.0, from 0.01% to 6% by weight of an antimicrobial agent selected from the group consisting of sorbic acid, benzoic acid, sodium benzoate, potassium sorbate, sodium sorbate, and potassium benzoate, and, from 0.001% to 45% (preferably 0.1% to 20%) by weight of the lactose-hydrolyzing enzyme to form a commercially sterilized enzyme composition. The dairy product is heated to a selected temperature for a time sufficient to at least pasteurize the dairy product; a selected quantity of the commercially sterile enzyme composition is combined with the pasteurized dairy product to produce an enzyme—dairy product combination containing from five to one hundred and fifty parts per million of the lactose-hydrolyzing enzyme; the enzyme—dairy product combination is packaged and frozen such that said lactose-hydrolyzing enzyme continues to hydrolyze lactose after the product combination is frozen; the packaged and frozen enzyme—dairy product combination is stored for a length of time sufficient to permit the enzyme to hydrolyze generally all lactose in the enzyme—dairy product combination prior to ingestion of the enzyme—dairy product combination by an individual; the product combination is thawed until it has the consistency of a conventional ice cream milk shake containing ice particles in a liquid matrix; and, the thawed product combination is served for ingestion by an individual. The packaged frozen product combination can be stored for a period of time in the range of two to fourteen days, or longer. The edible acid, buffer, and enzyme can be of the types earlier discussed herein.

As would be appreciated by those of skill in the art, the amount of water admixed with a dried enzyme powder composition to produce a water—enzyme powder solution can vary widely as desired. A water—enzyme powder solution can include 50% to 99% by weight water but preferably includes from 79% to 98% by weight water.

In a further embodiment of my invention, I provide a method for preparing a pasteurized lactose-containing ice cream product in which lactose is hydrolyzed prior to ingestion of the product by a lactose intolerant individual. The method includes the step of providing an ice cream mix including from 5% to 70% by weight milk; from zero to 20 percent by weight butterfat; from zero to fifty percent by weight cream; and, from one to seven percent by weight lactose. The method also includes the step of chemically commercially sterilizing an acid-sensitive lactose-hydrolyzing lactase enzyme by admixing from 50% to 99% by weight of water; from 0.1 to 6% by weight of an acidic component for adjusting the pH of the enzyme composition within the range of about 2.0 to 5.5; from 0.01% to 6% by weight of an antimicrobial agent selected from the group consisting of sorbic acid, benzoic acid, sodium benzoate, potassium sorbate, sodium sorbate, and potassium benzoate; and, from 0.001% to 45% by weight of the acid-sensitive lactose-hydrolyzing lactase enzyme to form a chemically sterile enzyme composition. The dairy product is heated to a selected temperature for a time sufficient to at least pasteurize the dairy product; a selected quantity of said chemically sterile enzyme composition is combined with said pasteurized dairy product to produce an enzyme—ice cream product containing from five parts per million to one thousand parts per million of said lactose-hydrolyzing acid-sensitive lactase enzyme; and, the enzyme—ice cream product is packaged and frozen. The enzyme—ice cream product can be frozen to a temperature of less than minus twenty degrees Fahrenheit. The enzyme can be a yeast-derived lactase enzyme; can continue to hydrolyze the lactose when the enzyme—ice cream product is at a temperature in the range of minus forty to minus twenty degrees Fahrenheit; and/or, can hydrolyze substantially all of the lactose in the enzyme—ice cream product in about three week. The chemically sterile enzyme composition is combined with the pasteurized dairy product within about ten minutes of admixing the lactase enzyme with the water, the antimicrobial agent and the acidic component.

In another embodiment of my invention, I provide a commercially sterile enzyme powder composition for combination with an ice cream mix which has been heated to a selected temperature for a time sufficient to at least pasteurize the ice cream mix. The enzyme composition hydrolyzes lactose to glucose and galactose. The enzyme composition includes from 4% to 20% by weight of an edible acidic component for adjusting the pH of the enzyme composition with the range of about 2.0 to 5.5 when the composition is hydrated; from 0.02% to 10% by weight of an antimicrobial agent selected from the group consisting of sorbic acid, benzoic acid, sodium benzoate, potassium sorbate, sodium sorbate, and potassium benzoate; and, from 14% to 93% by weight of an acid-sensitive lactose-hydrolyzing lactase. The enzyme powder composition can be hydrated and includes from 50% to 99% by weight of water.

In still a further embodiment of the invention, I provide an ice cream composition prepared to be frozen to hydrolyze lactose in the composition. The ice cream composition includes an ice cream mix including from 5% to 70% by weight milk; from zero to 20 percent by weight butterfat; from zero to fifty percent by weight cream; and, from one to seven percent by weight lactose. The ice cream composition also includes a sterilized lactose-hydrolyzing acid-sensitive lactase enzyme. The lactase enzyme can be admixed with the ice cream in a composition including from 50% to 99% by weight of water; from 0.1 to 6% by weight of an acidic component for adjusting the pH of the enzyme composition within the range of about 2.0 to 5.5; from 0.001% to 5% by weight of a buffer to facilitate maintenance of the pH in the range of 2.0 to 5.5; from 0.01% to 6% by weight of an antimicrobial agent selected from the group consisting of sorbic acid, benzoic acid, sodium benzoate, potassium sorbate, sodium sorbate, and potassium benzoate; and, from 0.001% to 45% by weight of the lactase enzyme.

The following examples depict the presently preferred embodiments of the invention for the purposes of illustrating the practice thereof and not by way of limitation of the scope of the invention. In the examples, all proportions are by weight, unless otherwise noted.

EXAMPLE 1

The following ingredients are provided.

| Component | Grams |
|---|---|
| LACTASE ENZYME (1) | 1000.00 |
| CITRIC ACID 1 HYDRATE (ACIDULANT) | 54.34 |
| POTASSIUM SORBATE (ANTI BACTERIAL AGENT) | 4.000 |
| DISODIUM PHOSPHATE-DIHYDRATED (BUFFER) | 36.819 |
| SODIUM LAURYL SULFATE | .500 |

-continued

| Component | Grams |
|---|---|
| (SURFACTANT) | |
| WATER (8.466 LB/GAL;<br>3840 GM/GAL; 3.84 L/GAL) | 14000.000 |
| TOTAL | 15095.659 |

(1) Beta-D-galactosidase galactrohydrolase enzyme (I.U.B.3.2.1.23) (hereafter "beta enzyme) from Solvay Enzymes, P.O. Box 4226, Elkhart, Indiana 46514-0026.

The beta enzyme contains bacteria, as do many commercially available enzymes. The water, potassium sorbate, disodium phosphate, and citric acid are blended together at room temperature to form a chemical sterilization mixture. The beta enzyme is then mixed with the chemical sterilization mixture to form a sterile enzyme composition. The resulting sterile enzyme composition has a pH of 4.51. The pH stability of the enzyme composition of the invention is increased by utilizing a buffer system which resists any change in the pH of the composition. In particular, the disodium phosphate increases the pH stability of the composition. While any desired buffer system can be utilized in the practice of the invention, sodium citrate, potassium salts, calcium salts, and/or sodium salts are, by way of example and not limitation, presently preferred. The 4.51 pH of the resulting aqueous enzyme composition is in the preferred pH range of 2.0 to 4.6.

EXAMPLE 2

Fifteen minutes after the hydrated enzyme composition of EXAMPLE 1 is produced, a plate count is performed to determine the presence of aerobic and anaerobic bacteria. The plate count is performed by transferring one milliliter of the enzyme composition to a 10 milliliter enriched Thio. The Thio is incubated at 35° C. for four days to culture for anaerobes. The Thio is then examined daily to determine the existence of aerobic and anaerobic bacteria. The forgoing plate count procedure is carried out in accordance with the FDA Bacteriological Analytical Manual, 4th Edition, 1984, Chapter 4, and with the ASM Manual of Clinical Microbiology, 4th Edition, 1985. In each plate count less than ten aerobic microorganisms (bacteria) per grams are detected. No anaerobic bacteria are detected during any of the plate counts.

EXAMPLE 3

Fifteen minutes after the hydrated enzyme composition of EXAMPLE 1 is produced, i.e., as soon as the rehydration of the powder is performed, about one milliliter of beta enzyme is extracted from the enzyme composition. A plate count is performed to determine the presence of aerobic and anaerobic bacteria. The plate count is performed by transferring the one milliliter of beta enzyme to a 10 milliliter enriched Thio. The Thio is incubated at 35° C. for four days to culture for anaerobes. The Thio is then examined daily to determine the existence of aerobic and anaerobic bacteria. The forgoing plate count procedure is carried out in accordance with the FDA Bacteriological Analytical Manual, 4th Edition, 1984, Chapter 4, and with the ASM Manual of Clinical Microbiology, 4th Edition, 1985. In each plate count less than ten aerobic microorganisms (bacteria) per grams are detected. No anaerobic bacteria are detected during any of the plate counts.

EXAMPLE 4

Four thousand gallons of pasteurized whole milk is provided. The milk contains about 4.5% by weight lactose. The 15095.159 grams of sterile enzyme composition from Example 1 is mixed with the 4000 gallons of pasteurized whole milk at room temperature to form about 4000 gallons of a milk—enzyme composition. The milk—enzyme composition is packaged in one gallon cartons. The one gallon cartons are refrigerated at 35 to 40 degrees Fahrenheit.

EXAMPLE 5

Twenty-four hours after the milk in Example 4 is prepared and packaged, milk from one of the refrigerated one gallon cartons is tested to determine the concentration of lactose. The milk contains about 3.0 percent by weight lactose.

EXAMPLE 6

Forty-eight hours after the milk in Example 4 is prepared and packaged, milk from one of the refrigerated one gallon cartons is tested to determine the concentration of lactose. The milk contains about 2.0 percent by weight lactose.

EXAMPLE 7

Seventy-two hours after the milk in Example 4 is prepared and packaged, milk from one of the refrigerated one gallon cartons is tested to determine the concentration of lactose. The milk contains about 1.0 percent by weight lactose.

EXAMPLE 8

Ninety-six hours after the milk in Example 4 is prepared and packaged, milk from one of the refrigerated one gallon cartons is tested to determine the concentration of lactose. The milk contains less than 0.09% by weight lactose.

EXAMPLE 9

Examples 1 to 8 are repeated, except that the amount of citric acid in the enzyme composition of Example 1 is decreased such that the pH of the resulting enzyme composition in Example 1 is about 5.1 instead of 4.51. Similar results are obtained.

EXAMPLE 10

Examples 1 to 8 are repeated, except that the amount of citric acid in the enzyme composition of Example 1 is increased such that the pH of the resulting enzyme composition in Example 1 is about 2.6 instead of 4.51. Similar results are obtained.

EXAMPLE 11

Examples 1 to 8 are repeated, except that 500 grams of beta enzyme are utilized in the aqueous enzyme composition of Example 1 instead of 1000 grams. Similar results are obtained except that the concentration of lactose determined in Examples 5 to 8 indicates that the lactose concentration is reduced more slowly than when only 454 grams of beta enzyme are utilized.

EXAMPLE 12

Examples 1 to 8 are repeated, except that fifty grams of disodium phosphate are utilized to make the aqueous enzyme composition of Example 1 instead of only 36.819 grams. Similar results are obtained.

EXAMPLE 13

Examples 1 to 8 are repeated, except that six grams of potassium sorbate is utilized to make the aqueous enzyme composition of Example 1 instead of only two grams. Similar results are obtained.

EXAMPLE 14

Examples 1 to 8 are repeated, except that two grams of sodium sorbate is utilized to make the aqueous enzyme composition of Example 1 instead of two grams of potassium sorbate. Similar results are obtained.

EXAMPLE 15

Examples 1 to 8 are repeated, except that 36.819 grams of sodium citrate is utilized in place of 36.819 grams of disodium phosphate to make the aqueous enzyme composition of Example 1. Similar results are obtained.

EXAMPLE 16

Examples 1 to 8 are repeated, except that 54.346 grams of lactic acid are used in place of 54.346 grams of citric acid to make the aqueous enzyme composition of Example 1. Similar results are obtained.

EXAMPLE 17

Examples 1 to 4 are repeated, except that in Example 4 the sterile enzyme composition is mixed with four thousand gallons of a pasteurized milk shake dairy mixture instead of four thousand gallons of pasteurized whole milk. Mixing the enzyme composition and the milk shake dairy mixture produces a milk shake—enzyme mixture. The pasteurized milk shake dairy mixture includes about 70% by weight whole milk; about 20% by weight sugar; about 7% by weight of a thickener like xanthan gum, locust bean gum, or guar gum; about 2% by weight of a stabilizer like monodiglyceride; and, about one percent by weight of vitamins and minerals. The whole milk contains about 4.5% by weight lactose. A variety of comparable formulations for making milk shake diary mixtures are well known in the art and will not be discussed in detail herein. Such mixtures, after being formulated, are typically refrigerated for ten to thirty hours, are frozen during a two to three day period, and are stored for weeks or months before they are purchased and thawed to form a viscous partially frozen milk shake drink having a consistency comparable to conventional vanilla or chocolate milk shakes sold by fast food restaurants like MCDONALDS, DAIRY QUEEN, BURGER KING, etc.

The cartons of the milk shake—enzyme mixture are refrigerated for twenty hours and are frozen by placing the cartons in a 25 degree Fahrenheit freezer for two to three days.

EXAMPLE 18

Twenty hours after the milk shake—enzyme mixture in Example 17 is prepared and packaged, and prior to its being frozen, milk shake—enzyme mixture from one of the refrigerated one gallon cartons is tested to determine the concentration of lactose. The milk shake—enzyme mixture contains about 2.5 percent by weight lactose.

EXAMPLE 19

Since, as noted in Example 17, the one gallon cartons are placed in a freezer twenty hours after the milk shake—enzyme mixture in Example 17 is prepared, the milk shake—enzyme mixture is partially frozen forty-eight hours following its preparation and packaging in Example 17. Forty-eight hours after the milk shake—enzyme mixture in Example 17 is prepared and packaged, partially frozen milk shake—enzyme mixture from one of the one gallon cartons is tested to determine the concentration of lactose. The partially frozen milk shake—enzyme mixture contains about 2.0 percent by weight lactose.

EXAMPLE 20

Since, as noted in Example 17, the one gallon cartons are placed in a freezer twenty hours after the milk shake—enzyme mixture in Example 17 is prepared, the milk shake—enzyme mixture is frozen seventy-two hours following its preparation and packaging in Example 17. Seventy-two hours after the milk shake—enzyme mixture in Example 4 is prepared and packaged, frozen milk shake—enzyme mixture from one of the one gallon cartons is tested to determine the concentration of lactose. The frozen milk shake—enzyme mixture contains about 1.5 percent by weight lactose.

EXAMPLE 21

Since, as noted in Example 17, the one gallon cartons are placed in a freezer twenty hours after the milk shake—enzyme mixture in Example 17 is prepared, the milk shake—enzyme mixture is still frozen one hundred and sixty-eight hours following its preparation and packaging in Example 17. One hundred and sixty-eight hours (two weeks) after the milk shake—enzyme mixture in Example 17 is prepared and packaged, frozen milk shake—enzyme mixture from one of the refrigerated one gallon cartons is tested to determine the concentration of lactose. The frozen milk shake—enzyme mixture contains less than about 0.05 percent by weight lactose.

EXAMPLE 22

Examples 17 to 21 are repeated, except that the amount of citric acid in the enzyme composition of Example 1 (i.e., the enzyme composition used in the milk shake—enzyme mixture of Examples 17 to 21) is decreased such that the pH of the resulting enzyme composition in Example 1 is about 5.1 instead of 4.51. Similar results are obtained.

EXAMPLE 23

Examples 17 to 21 are repeated, except that the amount of citric acid in the enzyme composition of Example 1 (i.e., the enzyme composition used in the milk shake—enzyme mixture of Examples 17 to 21) is increased such that the pH of the resulting enzyme composition in Example 1 is about 2.6 instead of 4.51. Similar results are obtained.

EXAMPLE 24

Examples 17 to 21 are repeated, except that 900 grams of lactase enzyme are utilized in the aqueous enzyme composition of Example 1 (i.e., the enzyme composition used in the milk shake—enzyme mixture of Examples 17 to 21) instead of only 454 grams. Similar results are obtained except that the concentration of lactose determined in Examples 18 to 21 indicates that the lactose concentration is reduced more quickly than when only 454 grams of lactase enzyme are utilized.

EXAMPLE 25

Examples 17 to 21 are repeated, except that fifty grams of disodium phosphate are utilized to make the aqueous enzyme composition of Example 1 (i.e., the enzyme composition used in the milk shake—enzyme mixture of Examples 17 to 21) instead of only 36.819 grams. Similar results are obtained.

EXAMPLE 26

Examples 17 to 21 are repeated, except that six grams of potassium sorbate is utilized to make the aqueous enzyme composition of Example 1 (i.e., the enzyme composition used in the milk shake—enzyme mixture of Examples 17 to 21) instead of only two grams. Similar results are obtained.

EXAMPLE 27

Examples 17 to 21 are repeated, except that two grams of sodium sorbate is utilized to make the aqueous enzyme composition of Example 1 (i.e., the enzyme composition used in the milk shake—enzyme mixture of Examples 17 to 21) instead of two grams of potassium sorbate. Similar results are obtained.

EXAMPLE 28

Examples 17 to 21 are repeated, except that 36.819 grams of sodium citrate is utilized in place of 36.819 grams of disodium phosphate to make the aqueous enzyme composition of Example 1 (i.e., the enzyme composition used in the milk shake—enzyme mixture of Examples 17 to 21). Similar results are obtained.

EXAMPLE 29

Examples 17 to 21 are repeated, except that 54.346 grams of lactic acid are used in place of 54.346 grams of citric acid to make the aqueous enzyme composition of Example 1 (i.e., the enzyme composition used in the milk shake—enzyme mixture of Examples 17 to 21). Similar results are obtained.

EXAMPLE 30

Examples 1 to 8 are repeated, except that 1000 grams of lactase enzyme are utilized in the aqueous enzyme composition of Example 1 instead of 1000 grams of beta enzyme. Similar results are obtained.

EXAMPLE 30

Examples 1 to 8 are repeated, except that 1000 grams of protease enzyme are utilized in the aqueous enzyme composition of Example 1 instead of 1000 grams of beta enzyme. Similar results are obtained.

EXAMPLE 31

The following ingredients are provided.

| Component | Pounds |
|---|---|
| LACTASE ENZYME (Yeast derived)(1) | 2.20 |
| CITRIC ACID 1 HYDRATE (ACIDULANT) | 0.05 |
| POTASSIUM SORBATE (ANTI BACTERIAL | 0.110 |

-continued

| Component | Pounds |
|---|---|
| AGENT) | |
| WATER (8.466 LB/GAL; 3840 GM/GAL; 3.84 L/GAL) | 42.000 |
| TOTAL | 44.365 |

(1)Solvay Enzymes, P.O. Box 4226, Elkhart, Indiana 46514-0026. The lactase enzyme is derived from the controlled fermentation of the yeast *Kluyveromyces lactis*. Solvay Enzymes noted that this enzyme was acid sensitive and was intended for use only at a pH between 6 and 8. It recommended that the enzyme not be utilized at a pH below 6 because the enzyme rapidly lost its effectiveness below a pH of 6. Solvay Enzymes also predicted that the enzyme would not function whenused as described in this and the following examples to hydrolyze lactose.

The water, potassium sorbate, and citric acid are blended together at room temperature to form a chemical sterilization mixture. The lactase enzyme is then mixed with the chemical sterilization mixture to form a sterile enzyme composition. The resulting sterile enzyme composition has a pH of about 4.5. The pH stability of the enzyme composition of the invention can, if desired, be increased by utilizing a buffer system which resists any change in the pH of the composition. In particular, disodium phosphate would increase the pH stability of the composition. While any desired buffer system could be utilized in the practice of the invention, sodium citrate, potassium salts, calcium salts, and/or sodium salts are, by way of example and not limitation, presently preferred. The 4.5 pH of the resulting aqueous enzyme composition is in the desired pH range of 2.0 to 5.5, preferably 2.5 to 5.1, for sterile enzyme compositions utilized in preparing ice cream in accordance with the invention. As used herein, ice cream comprises a frozen dairy product including 5% to 70% by weight milk (in either liquid or dry (powder) form), zero to 50% by weight cream, one to seven percent by weight lactose, zero to 20% by weight butterfat or other fat, and five to 35% by weight sugar. Ice cream can also, if desired, include stabilizers, flavoring, preservatives, and other components found in ice cream prepared in accordance with the prior art. Examples of ice cream include sherbet, ice milk, and ice creams including varying proportions of butterfat or other fat substitutes. The process described in this Example 31 is one procedure for producing sterilized lactase enzyme. Sterilized lactase enzyme can also be produced by filtering the enzyme to remove bacteria and other contaminants.

EXAMPLE 32

Five minutes after the hydrated enzyme composition of EXAMPLE 31 is produced, a plate count is performed to determine the presence of aerobic and anaerobic bacteria. The plate count is performed by transferring one milliliter of the enzyme composition to a 10 milliliter enriched Thio. The Thio is incubated at 35° C. for four days to culture for anaerobes. The Thio is then examined daily to determine the existence of aerobic and anaerobic bacteria. The forgoing plate count procedure is carried out in accordance with the FDA Bacteriological Analytical Manual, 4th Edition, 1984, Chapter 4, and with the ASM Manual of Clinical Microbiology, 4th Edition, 1985. In each plate count less than ten aerobic microorganisms (bacteria) per grams are detected. No anaerobic bacteria are detected during any of the plate counts.

EXAMPLE 33

Five minutes after the hydrated enzyme composition of EXAMPLE 31 is produced, i.e., as soon as the rehydration of the powder is performed, about one milliliter of lactase enzyme is extracted from the enzyme composition. A plate count is performed to determine the presence of aerobic and anaerobic bacteria. The plate count is performed by transferring the one milliliter of beta enzyme to a 10 milliliter enriched Thio. The Thio is incubated at 35° C. for four days to culture for anaerobes. The Thio is then examined daily to determine the existence of aerobic and anaerobic bacteria. The forgoing plate count procedure is carried out in accordance with the FDA Bacteriological Analytical Manual, 4th Edition, 1984, Chapter 4, and with the ASM Manual of Clinical Microbiology, 4th Edition, 1985. In each plate count less than ten aerobic microorganisms (bacteria) per grams are detected. No anaerobic bacteria are detected during any of the plate counts.

EXAMPLE 34

The following ingredients are mixed together to produce a vanilla ice cream mix which has about 14% butterfat:

| Component | Pounds |
| --- | --- |
| Milk, 3.25% butterfat | 3731.000 |
| Cream, 40% butterfat | 2800.350 |
| Milk (cow, dry, skim, non-fat) | 240.030 |
| Cane Syrup | 1155.700 |
| Corn Syrup | 900.557 |
| Ultra High Stabilizer | 26.670 |
| Artificial Vanilla Flavor | 62.230 |

EXAMPLE 35

The pasteurized vanilla ice cream mix of Example 34 is mixed together with the enzyme composition of Example 31. The enzyme composition of Example 31 is mixed together with the pasteurized ice cream mix of Example 34 within about 10 minutes, preferably within about three to five minutes, of adding the lactase enzyme to the chemical sterilization mixture. If the lactase enzyme is permitted to remain in the chemical sterilization mixture for more than about ten minutes, the lactase enzyme may be inactivated. After the vanilla ice cream mix of Example 34 is mixed together with the enzyme composition of Example 31, the following enzyme—ice cream composition is produced:

| Component | Weight % |
| --- | --- |
| Milk, 3.25% butterfat | 41.6364 |
| Cream, 40% butterfat | 31.2508 |
| Milk (cow, dry, skim, nonfat) | 2.6786 |
| Cane Syrup | 12.8971 |
| Corn Syrup | 10.0498 |
| Ultra High Stabilizer | 0.2976 |
| Artificial Vanilla Flavor | 0.6945 |
| LACTASE ENZYME (Yeast derived)(1) | 0.0246 |
| CITRIC ACID 1 HYDRATE (ACIDULANT) | 0.0006 |
| POTASSIUM SORBATE (ANTI BACTERIAL AGENT) | 0.0012 |
| WATER (8.466 LB/GAL; 3840 GM/GAL; 3.84 L/GAL) | 0.4687 |
| TOTAL | 100.0000 |

The enzyme—ice cream composition contains about 2.2% by weight lactose. After the enzyme—ice cream composition is prepared it is frozen at a temperature of minus forty degrees Fahrenheit. While the enzyme—ice cream composition can be frozen at any temperature under thirty-two degrees Fahrenheit, a freezing temperature of minus twenty degrees or less is preferred because at such low temperatures the size of ice crystals in the ice cream apparently is minimized.

EXAMPLE 36

One week after the enzyme—ice cream composition of Example 35 is frozen, a small portion of the ice cream is tested to determine the concentration of lactose. The ice cream contains about 1.8 percent by weight lactose.

EXAMPLE 37

Two weeks after the enzyme—ice cream composition of Example 35 is frozen, a small portion of the ice cream is tested to determine the concentration of lactose. The ice cream contains about 1.4 percent by weight lactose.

EXAMPLE 38

Three weeks after the enzyme—ice cream composition of Example 35 is frozen, a small portion of the ice cream is tested to determine the concentration of lactose. The ice cream contains no lactose. The lactose has been completely hydrolyzed by the lactase enzyme. In view of the warning by Solvay Enzymes that the yeast derived lactase enzyme would not function, this was a surprising and unexpected result, both to the extent that the enzyme continued to hydrolyze lactose at such a low temperature and to the extent that the lactase enzyme completely hydrolyzed the lactose in the ice cream. As used herein, an acid-sensitive enzyme is an enzyme the function of which is adversely affected when the enzyme is in a composition having an acidic pH. Acid-sensitive enzymes ordinarily at utilized in compositions having a pH of 6.0 or greater, preferably 7.0 or greater.

EXAMPLE 39

Examples 31 to 38 are repeated, except that 2.20 pounds of a fungal lactase enzyme derived by using aspergillus oryzae is utilized in place of the 2.20 pounds of the yeast derived lactase. Similar results are obtained except that:

1. In Example 36, the ice cream contains 1.5% by weight lactose.
2. In Example 37, the ice cream contains 1.5% by weight lactose.
3. In Example 38, the ice cream contains 1.0% by weight lactose.

Consequently, while the acid sensitive yeast-derived lactase completely hydrolyzed all of the lactose in three weeks, the fungal lactose did not. This was another surprising and unexpected result because the fungal lactose is acid tolerant and is intended to be utilized in compositions having an acidic pH.

EXAMPLE 40

Examples 31 to 40 are repeated, except that the amount of citric acid in the enzyme composition of Example 31 is decreased such that the pH of the resulting enzyme composition in Example 31 is about 5.1 instead of 4.5. Similar results are obtained.

EXAMPLE 41

Examples 31 to 40 are repeated, except that the amount of citric acid in the enzyme composition of Example 31 is increased such that the pH of the resulting enzyme composition in Example 1 is about 2.6 instead of 4.5. Similar results are obtained.

EXAMPLE 42

Examples 31 to 40 are repeated, except that 1.1 pounds of lactase enzyme is utilized in Example 31 instead of 2.2 pounds. Similar results are obtained except that the concentration of lactose determined in Examples 36 to 38 indicates that the lactose concentration is reduced more slowly than when 2.2 pounds of lactase enzyme are utilized.

EXAMPLE 43

Examples 31 to 40 are repeated, except that 0.33 pounds of potassium sorbate is utilized to make the sterile enzyme composition of Example 31 instead of only 0.11 pounds. Similar results are obtained.

EXAMPLE 44

Examples 31 to 40 are repeated, except that 2.2 pounds of sodium sorbate is utilized to make the sterile enzyme composition of Example 31 instead of 2.2 pounds of potassium sorbate. Similar results are obtained.

EXAMPLE 45

Examples 31 to 40 are repeated, except that 0.055 pounds of lactic acid are used in place of 0.055 pounds of citric acid to make the sterile enzyme composition of Example 31. Similar results are obtained.

EXAMPLE 46

Examples 31 to 40 are repeated, except that in Example 35 5731.35 pounds of milk with zero percent butterfat is utilized in place of the 3731.000 pounds of milk having 3.25% butterfat and the cream having 40% butterfat. Similar results are obtained.

Having described my invention in such terms as to enable those skilled in the art to understand and practice it, and having identified the presently preferred embodiments thereof, I claim:

1. A method for preparing a pasteurized lactose-containing ice cream product in which lactose is hydrolyzed prior to ingestion of the product by a lactose intolerant individual, said method including the steps of
   (a) providing a dairy product comprising an ice cream mix including
       (i) from 5% to 70% by weight milk,
       (ii) from zero to 20 percent by weight butterfat,
       (iii) from zero to fifty percent by weight cream, and
       (iv) from one to seven percent by weight lactose;
   (b) commercially sterilizing a lactose-hydrolyzing acid-sensitive lactase enzyme;
   (c) heating the dairy product to a selected temperature for a time sufficient to at least pasteurize the dairy product;
   (d) combining a selected quantity of said commercially sterilized lactose-hydrolyzing lactase enzyme with said pasteurized dairy product to produce an enzyme—ice cream product combination containing from five parts per million to one thousand parts per million of said lactose-hydrolyzing lactase enzyme;
   (e) packaging and freezing said enzyme—ice cream product combination wherein said enzyme—ice cream product is frozen to a temperature of less than minus twenty degrees Fahrenheit, and said enzyme continues to hydrolyze said lactose at said temperature.

2. The method of claim 1 wherein said enzyme is a yeast-derived lactase enzyme.

3. The method of claim 1 wherein said enzyme is an acid sensitive lactase enzyme and said enzyme continues to hydrolyze said lactose when said enzyme—ice cream product is at a temperature in the range of minus forty to minus twenty degrees Fahrenheit.

4. The method of claim 3 wherein said lactase enzyme hydrolyzes substantially all of the lactose in said enzyme—ice cream product in about three weeks.

5. The method of claim 1 wherein
   (a) said lactase enzyme is sterilized by preparing a composition including
       (i) from 50% to 99% by weight of water,
       (ii) from 0.1 to 6% by weight of an acidic component for adjusting the pH of the enzyme composition within the range of about 2.0 to 5.5,
       (iii) from 0.01% to 6% by weight of an antimicrobial agent selected from the group consisting of sorbic acid, benzoic acid, sodium benzoate, potassium sorbate, sodium sorbate, and potassium benzoate, and,
       (iv) from 0.001% to 45% by weight of said lactase enzyme; and, (b) in step (d) said commercially sterilized lactose-hydrolyzing lactase enzyme is combined with said pasteurized dairy product within about ten minutes of admixing said acid sensitive lactase enzyme with said water, said antimicrobial agent, and said acidic component.

6. An ice cream composition prepared to be frozen to hydrolyze lactose in said composition, said composition including
   (a) an ice cream mix including
       (i) from 5% to 70% by weight milk,
       (ii) from zero to 20 percent by weight butterfat,
       (iii) from zero to fifty percent by weight cream, and
       (iv) from one to seven percent by weight lactose; and,
   (b) a sterilized lactose-hydrolyzing acid-sensitive lactase enzyme wherein said lactase enzyme is admixed with said ice cream mix in a composition including
       (I) from 50% to 99% by weight of water,
       (ii) from 0.1 to 6% by weight of an edible acidic component for adjusting the pH of the enzyme composition within the range of about 2.0 to 5.5,
       (iii) from 0.001% to 5% by weight of a buffer to facilitate maintenance of the pH in the range of 2.0 to 5.5,
       (iv) from 0.01% to 6% by weight of an antimicrobial agent selected from the group consisting of sorbic acid, benzoic acid, sodium benzoate, potassium sorbate, sodium sorbate, and potassium benzoate, and,
       (v) from 0.001% to 45% by weight of said lactase enzyme.

* * * * *